ns patent
United States Patent [19]
Loeb et al.

[11] 4,002,688
[45] Jan. 11, 1977

[54] PROCESS FOR CRYSTALLIZING 2,2-BIS[3,5-DIBROMO-4-(2-HYDROXYE-THOXY)PHENYL] PROPANE

[75] Inventors: Barry L. Loeb; Kenneth J. Witsken, both of Cincinnati, Ohio

[73] Assignee: Emery Industries, Inc., Cincinnati, Ohio

[22] Filed: Mar. 28, 1975

[21] Appl. No.: 563,254

[52] U.S. Cl. .................................. 260/613 R
[51] Int. Cl.² ................................. C07C 41/12
[58] Field of Search ....................... 260/613 R

[56] References Cited
UNITED STATES PATENTS 3,794,617  2/1974  Mains et al. ............ 260/613 R X

OTHER PUBLICATIONS

Weissberger, Separation & Purification, Part I (1956), pp. 482–485.
Siegel, Process Machinery, 2nd ed. (1953), pp. 437–439.

Primary Examiner—Bernard Helfin
Attorney, Agent, or Firm—Gerald A. Baracka; John D. Rice

[57] ABSTRACT

The present process relates to the production of crystalline 2,2-bis[3,5-dibromo-4-(2-hydroxyethoxy)phenyl] propane by cooling the molten material with shear. An especially useful aspect of this invention involves the continuous crystallization of 2,2-bis[3,5-dibromo-4-(2-hydroxyethoxy)phenyl] propane employing a scraped surface heat exchanger to achieve the desired rate of cooling and shear.

6 Claims, No Drawings

PROCESS FOR CRYSTALLIZING 2,2-BIS[3,5-DIBROMO-4-(2-HYDROXYETHOXY)-PHENYL] PROPANE

BACKGROUND OF THE INVENTION 2,2-Bis[3,5-dibromo-4-(2-hydroxyethoxy)phenyl] propane is recognized to be an effective flame retardant for numerous polymers including polycarbonates, polyurethanes, polyesters, copolyesters and the like. The compound can be blended with the polymer or employed as a coreactant and incorporated into the polymer structure.

One of the major drawbacks to the use of 2,2-bis[3,5-dibromo-4-(2-hydroxyethoxy)phenyl] propane is the difficulty in obtaining the product in crystalline form. Conventional recovery processes produce the amorphous (non-crystalline) form of the product. While it is possible to flake or powder the amorphous material, upon storage at temperatures above about 30° C the product "slumps" to form a solid mass. For most uses this requires that the product be reground or otherwise processed to put the 2,2-bis[3,5-dibromo-4-(2-hydroxyethoxy)phenyl] propane in a form suitable for handling. The crystalline form on the other hand, does not slump and once flaked or powdered will remain indefinitely in the free-flowing condition as long as the temperature does not exceed the melt point of the material (115°–120° C).

In the past there has been no completely acceptable means to rapidly crystallize 2,2-bis[3,5-dibromo-4-(2-hydroxyethoxy)phenyl] propane, especially when large quantities of material are involved. While it is possible to achieve crystallization by aging the material in small containers (up to about 50 pounds) for a week or more at 50° to 75° C, this technique is commercially unacceptable because of heat, space and time requirements. It would be highly advantageous and useful if a process were available to rapidly and economically crystallize 2,2-bis[3,5-dibromo-4-(2-hydroxyethoxy)phenyl] propane. It would be even more desirable if such a process was adaptable to continuous or semi-continuous operation.

SUMMARY OF THE INVENTION

We have now quite unexpectedly discovered a process for the production of crystalline 2,2-bis[3,5-dibromo-4-(2-hydroxyethoxy)phenyl] propane. Employing the process of this invention, it is possible to conveniently and economically convert amorphous 2,2-bis[3,5-dibromo-4-(2-hydroxyethoxy) phenyl] propane to the crystalline form. This is accomplished by cooling molten 2,2-bis[3,5-dibromo-4-(2-hydroxyethoxy)phenyl] propane while simultaneously applying shear to the viscous melt. The process of this invention can also be used to directly produce crystalline 2,2-bis[3,5-dibromo-4-(2-hydroxyethoxy)phenyl] propane from a melt obtained from a manufacturing operation. In this case the melt is usually stripped to remove undesirable impurities before being processed to obtain the desired crystalline form of the product. The present process is particularly advantageous since it utilizes conventional processing equipment and is readily adaptable to production of crystalline 2,2-bis[3,5-dibromo-4-(2-hydroxyethoxy)phenyl] propane on a continuous or semi-continuous basis.

We have found that by cooling a melt of 2,2-bis[3,5-dibromo-4-(2-hydroxyethoxy)phenyl] propane with the simultaneous application of shear it is possible to selectively produce the crystalline form of the product. More specifically, a 90° C to 140° C melt of the 2,2-bis[3,5-dibromo-4-(2-hydroxyethoxy)phenyl] propane is cooled 10° to 40° C with the application of shearing work at the rate of 25,000 to 66,000 joules per kilogram and, more preferably, from 35,000 to 57,000 joules/kg. The melt is exposed to the cool/shear conditions for at least 0.5 minute and, more preferably, for one to five minutes. For efficient crystallization the 2,2-bis[3,5-dibromo-4-(2-hydroxyethoxy)phenyl] propane should contain predominantly the diethoxylated product and preferably will be 85% diethoxylate and contain less than about 1% by weight solvent and water impurities.

The above conditions are advantageously achieved by the preferred embodiment of this invention, which comprises continuously feeding the melt through a scraped surface heat exchanger at a rate of 400 to 1100 kilograms per hour per square meter of cooling surface. The exchanger is cooled with a liquid coolant maintained at a temperature of about 70° to 95° C. Shear is obtained by developing an internal pressure from 2 atmospheres up to about 17 atmospheres and, more preferably between about 3 and 14 atmospheres within the exchanger. This is accomplished by locating a back pressure control valve or the like at the outlet of the exchanger to restrict the flow of the viscous melt exiting the exchanger.

DETAILED DESCRIPTION

The present invention relates to the production of crystalline 2,2-bis[3,5-dibromo-4-(2-hydroxyethoxy)-phenyl] propane. In its broadest sense the process involves cooling a melt of 2,2-bis[3,5-dibromo-4-(2-hydroxethoxy)phenyl] propane while simultaneously applying a shearing force to selectively obtain the crystalline form of the product. In a preferred ebmodiment capable of rapidly crystallizing large amounts of 2,2-bis[3,5-dibromo-4-(2-hydroxyethoxy)phenyl] propane on a continuous basis, cooling and shear are achieved using a scraped surface heat exchanger.

The 2,2-bis[3,5-dibromo-4-(2-hydroxyethoxy)phenyl] propane used in the process of this invention is prepared according to known procedures. Generally, it is obtained by ethoxylating 4,4'-isopropylidene(2,6-dibromo-phenol), commonly referred to as tetrabromobisphenol A, obtained from the bromination of bisphenol A. In conducting the ethoxylation reaction, tetrabromobisphenol A is condensed with ethylene oxide in the presence of a basic catalyst. The reaction can be conducted with or without solvents but usually the tetrabromobisphenol A is dissolved in a hydrocarbon solvent, such as xylene, and charged to the reactor with the catalyst. Catalyst levels can vary but will generally be between about 0.05 and 0.2% by weight based on the tetrabromobisphenol A. Reaction conditions may be varied depending on the catalyst used and the rate of reaction desired. Reaction temperatures can range from 130° to 170° C or higher while pressures can be varied from about 1.7 up to about 7 atmospheres or more. The reaction is monitored by determining the amount of unreacted phenol which is conveniently accomplished by titrating samples drawn from the reactor with a standardized base solution using a phenolphthalein indicator. In a typical procedure, after azeotropically removing any water introduced with the catalyst or solvent from the system the reactor is heated to about 150° C, vented to about 0.7 atmosphere and ethylene oxide charged to a pressure of 3.5 atmospheres. The reaction temperature is maintained and additional ethylene oxide is charged to maintain the pressure of about 3.5 atmospheres until the reaction is terminated, usually when the acid value of the reaction mixture is less than about two.

With this process it is possible to selectively produce crystalline 2,2-bis[3,5-dibromo-4-(2-hydroxyethoxy)phenyl] propane from the melt by controlling the cooling rate and rate of shear. To obtain crystallization the product being treated should be relatively free of impurities and consist predominantly of the diethoxylated product. Diethoxylate, for the purpose of this invention and as used herein, is defined as the product having one ethylene oxide unit condensed at each of the available phenol groups of the tetrabromobisphenol A. The diethoxylate has the structural formula

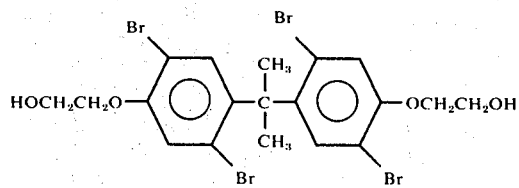

Unreacted tetrabromobisphenol A, mono-, tri- and higher ethoxylated products should not exceed about 15% by weight of the product being processed. Also, for efficient crystallization solvent and water impurities should not exceed about 1% by weight of the 2,2-bis[3,5-dibromo-4-(2-hydroxyethoxy)phenyl] propane. For this reason the 2,2-bis[3,5-dibromo-4-(2-hydroxyethoxy)phenyl] propane is usually stripped, i.e. distilled under vacuum, prior to crystallization to remove solvent and any water carried over from the manufacturing operation. For best results, the material being crystallized should contain 93 wt. % or more diethoxylate and less than 0.5% by weight solvent and water impurities.

To produce crystalline 2,2-bis[3,5-dibromo-4-(2-hydroxyethoxy)phenyl] propane a melt of the product is cooled with the application of shear. The method of cooling and the application of shear work is not critical to the process and crystallization can be achieved without regard to the particular type or arrangement of equipment as long as the specified shear/cooling relationship is satisfied. In the process a melt of 2,2-bis[3,5-dibromo-4-(2-hydroxyethoxy)phenyl] propane in the temperature range 90° C to 140° C is cooled 10° C to 40° C while simultaneously applying a shear force of 25,000 to 60,000 joules per kilogram and, more preferably, 35,000 to 57,000 joules/kg. Excellent results are obtained when the initial temperature of the melt is between 105° and 120° C and the temperature is decreased 15° to 30° C in the processing. The length of exposure (residence time if the process is conducted on a continuous basis) to the cooling and shear conditions will generally exceed about 0.5 minute and more generally will be between one and five minutes. While from the standpoint of obtaining a crystalline product there is no upper limit to the length of time required to obtain the necessary temperature decrease in the melt, from a practical point of view the process will be conducted in as short a time as possible, particularly when the process is used to continuously crystallize the 2,2-bis[3,5-dibromo-4-(2-hydroxyethoxy)phenyl] propane.

In accordance with the process of this invention, amorphous 2,2-bis[3,5-dibromo-4-(2-hydroxyethoxy)phenyl] propane can be converted to the crystalline form by melting the amorphous material to 90° to 140° C and subjecting the melt to the specified cool/shear conditions. The process can also be used to directly recover the crystalline form of 2,2-bis[3,5-dibromo-4-(2-hydroxyethoxy)phenyl] propane from known reaction procedures, such as from the reaction of ethylene oxide and tetrabromobisphenol A. In the latter situation, the reaction mixture containing the 2,2-bis[3,5-dibromo-4-(2-hydroxyethoyx)phenyl] propane is stripped prior to crystalliaztion to remove solvent, water and other undesirable reaction products which could interfere with crystallization. Since the temperature used for stripping can range up to 200° C or higher, additional cooling is required to reduce the melt to the 90°–140° C temperature range necessary for crystallizing. This additional cooling requirement or preliminary cooling, to be distinquished from the cooling during the crystallizing process in the presence of shear, can be conveniently accomplished in a number of ways which will be evident to one skilled in the art. The preliminary cooling can be achieved independent of crystallization process and equipment, or if the equipment has sufficient cooling capacity for both preliminary cooling and cooling of crystallization, in conjunction therewith. Using this latter approach, however, it is necessary that the cooling, shear and residence time requirements are satisfied after the preliminary cooling is completed. The product can be cooled to the desired processing temperature prior to commencement of the crystallization in the stripper or it is possible to provide a suitable storage or holdup tank for this purpose. Alternatively, a heat exchanger can be inserted in the product line between the stripper and the equipment employed for crystallization.

Crystalline 2,2-bis[3,5-dibromo-4-(2-hydroxyethoxy)phenyl] propane is readily obtained by the above-described procedure. The crystalline product, having a sharp melting point in the range 115° to 120° C, can be stored for prolonged periods without reverting to the amorphous state. If allowed to melt, however, the product will revert to the amorphous form unless, of course, the product is once again crystallized.

In conducting this process it is not necessary that the 2,2-bis[3,5-dibromo-4-(2-hydroxyethoxy)phenyl] propane be completely crystallized prior to removal from the processing equipment wherein the required cooling and shear conditions are simultaneously obtained. Once crystallization is begun it will continue even though the rate may be less than optimum. This feature makes it possible, and in fact advantageous, to remove the melt from the cool/shear environment at some point prior to complete crystallization. The melt is then allowed to further cool to complete the crystallizing process. If desired, the product may also be oven-aged at about 50°–70° C for about a day to insure complete crystallization. Since the melt becomes progressively more viscous as it is cooled and as crystallization progresses removal of the product prior to complete crystallization, i.e. before solidification, facilitates handling, reduces power consumption and permits high throughputs with the equipment. It also makes the process useful for continuous or semi-continuous operations.

In a preferred embodiment of this invention a scraped surface heat exchanger is used to control the rate of cooling and rate of shear. Such processes are particularly useful since they are adaptable to continuous and semi-continuous crystallization of 2,2-bis[3,5-dibromo-4-(2-hydroxyethoxy)phenyl] propane and are capable of high throughputs. Conventional scraped surface heat exchangers used to process viscous products and to transfer heat by bringing a heated product into direct contact with a cooled surface while continuously scraping or cleaning the material from the heat transfer walls can be used. These exchangers can be either horizontally or vertically mounted units capable of withstanding internal pressures up to about 35 atmospheres and are equipped with a cooling jacket for use with liquid coolants and an electric or hydraulic drive to develop shaft speeds up to about 800 rpm, and more usually from 150 to 600 rpm. The exchanger can have either circular or oval heat transfer walls and the shaft (rotor) can be arranged to operate either concentrically or eccentrically with either fixed scraping blades or floating or spring-loaded blades.

To conduct the preferred process of this invention the molten 2,2-bis[3,5-dibromo-4-(2-hydroxyethoxy)phenyl] propane, at a temperature within the already defined limits, is passed through the scraped surface heat exchanger at a rate of 400 to 1100 kilograms per hour per square meter of cooling surface and, more preferably, at a rate of about 450 to 700 kg/hr m² of cooling surface. The melt is pumped using conventional pumping means such as a positive displacement pump, reciprocating-, gear-, or screw-type pumps, etc. capable of maintaining the above rate of flow and developing an internal pressure from about 2 up to about 17 atmospheres within the exchanger. Internal pressure is developed by means of a back pressure control valve or similar device at the outlet which can be throttled to impede or restrict the flow of the 2,2-bis[3,5-dibromo-4-(2-hydroxyethoxy)phenyl] propane exiting the exchanger. The amount of shear applied to the melt is maintained within the desired limits by controlling the back pressure within the heat exchanger. Excellent crystallization is obtained with this process when the initial temperature of the melt entering the exchanger is 105°–120° C, the pressure within the exchanger is between 3 and 14 atmospheres and the temperature of the melt is lowered 15°–30° C. The residence time $$\left(\frac{\text{useful volume of the equipment}}{\text{processing rate}}\right)$$

will generally exceed 0.5 minute and more usually will range from one to five minutes. The heat exchanger is cooled with a suitable liquid coolant maintained at 70° to 95° C and, more preferably, 75° to 85° C. Any of the commonly used heat transfer media which are fluids above about 65° C can be used, however, water is typically used in commercial operations. The rate of cooling for a given throughput is controlled by the temperature and/or rate of flow of the coolant.

In a typical continuous operation of this type the product exiting the exchanger has a paste-like consistency and has a temperature between about 85° C and 105° C. At this stage in the processing crystallization has begun to occur within the melt and will continue outside the exchanger as the 2,2-bis[3,5-dibromo-4-(2-hydroxyethoxy)phenyl] propane cools further. The viscous paste can be spread into pans, trays or on a continuously moving belt or the like using suitable spreading means and allowed to cool, generally to about 50° C or lower, until the 2,2-bis[3,5-dibromo-4-(2-hydroxyethoxy)phenyl] propane is sufficiently crystallized so that the product can be crushed, flaked or otherwise treated to put the material in form suitable for handling.

The significance of the invention is better appreciated by a consideration of the following examples which are not intended to limit the scope of the invention but are provided only by way of illustration. As will be evident to those skilled in the art, certain details of the process can be varied without departing from the spirit and scope of the invention. In the examples all parts and percentages are given on a weight basis unless otherwise indicated.

To distinquish between the amorphous and crystalline form of the product a differential scanning calorimeter is employed. A 0.015 – 0.02 gram sample of the product is heated in an open aluminum cup under a flow of nitrogen (60–70 mls/min.) at a rate of 10° C/min. Employing these conditions, crystalline 2,2-bis[3,5-dibromo-4-(2-hydroxyethoxy)phenyl] propane exhibits a sharp endotherm commencing at about 114°–115° C and peaking at about 117° C. With the amorphous 2,2-bis[3,5-dibromo-4-(2-hydroxyethoxy)phenyl] propane, however, an exotherm is present at about 35°–45° C and peaks at about 60°–80° C before recovering and giving the usual melting point endotherm. This test provides a rapid and convenient means to determine whether the product is crystalline or amorphous, or the extent of crystallinity, and is readily adaptable to commercial operations where quick analysis is essential. Other techniques can also be used for this purpose. One such test is to allow a weighted sample of the powdered or flaked product to stand in a cylindrical tube at 60° C to determine whether the material fuses or remains flowable after a specified period of time.

EXAMPLE I 2,2-Bis[3,5-dibromo-4-(2-hydroxyethoxy)phenyl] propane was prepared by the reaction of two mols ethylene oxide with one mol tetrabromobisphenol A in xylene with a basic catalyst. The product was vacuum distilled at 150° C and 10 mm Hg. and allowed to cool to room temperature. The clear, brittle solid product contained about 96% diethoxylate (determined by liquid chromotographic anaylsis) and was shown by differential scanning calorimetric analysis to be in the amorphous form as evidenced by the appearance of a pronounced exotherm peaking at about 70° C. The amorphous 2,2-bis[3,5-dibromo-4-(2-hydroxyethoxy)phenyl] propane was then heated to about 120° C and closed to about 90° C over a period of about two minutes while applying a shearing force of about 40,000 joules/kg by vigorously agitating the mass. Analysis of the resulting product by differential scanning calorimetry after cooling to room temperature indicated that the material had been converted to the crystalline form. The opaque, whitish product had a sharp melting point of 117°–118° C.

When the above example was repeated employing identical conditions except that the agitation was reduced so that the shear applied while the melt cooled from 120° C to 90° C was only 15,000 joules per kilogram, a crystalline product was not obtained. Similarly crystalline 2,2-bis[3,5-dibromo-4-(2-hydroxyethoxy)-phenyl] propane could not be produced when the product was exposed to the shearing conditions for only 25 seconds or when a melt at 150° C was cooled with shear to 120° C and cooling continued without shear to the solidification point.

EXAMPLE II

Ethylene oxide (two mols) and tetrabromobisphenol A (one mol) were reacted at a pressure of about 3.5 atmospheres in xylene using a basic catalyst. When the reaction was completed (acid value <2) the reaction mixture was stripped at about 150° C and 10 mm Hg and cooled to about 110° C in the stripping vessel. This melt was then pumped at a rate of 545 kg/hr through an electrically driven horizontal concentric floating blade-type scraped surface heat exchanger having 0.84 m² of cooling surface. A back pressure control valve located at the outlet of the exchanger was throttled to develop an internal pressure of about 17 atmospheres. Operating the exchanger at a constant shaft speed and at about 80% of full load (determined by measuring the current load with an ammeter) the temperature of the melt was decreased about 21° C in a single pass through the unit while applying a shear force of about 43,000 joules/kg. Cooling was achieved by pumping 75° C water through the cooling jacket at a flow sufficient to obtain this cooling rate. The exiting viscous paste was deposited on a continuously moving belt, spread into a thin uniform sheet and allowed to cool to about 40° C. The opaque white product was then flaked off the belt into containers suitable for storage. Analysis of the fully processed product by differential scanning calorimetry showed no evidence of the exotherm present with amorphous 2,2-bis[3,5-dibromo-4-(2-hydroxyethoxy)phenyl] propane. The single heat transistion was a sharp endotherm peaking at 117° C, indicating the product had been crystallized. The 2,2-bis[3,5-dibromo-4-(2-hydroxyethoxy)phenyl] propane, in addition to having a melt point of 117°–118° C, had an acid value of 1.8, hydroxyl value of 181 and contained 49.2% bromine. Flakes of this material retained their flowability even after prolonged storage in lots as large as 2000 pounds and could be readily incorporated into polyesters and copolyesters by blending or by polymerization to impart superior flame retardant properties.

EXAMPLES III – IV

To demonstrate the versatility of the process and the ability to obtain crystalline 2,2-bis[3,5-dibromo-4-(2-hydroxyethoxy)phenyl] propane employing different operating conditions, Example II was repeated with the following variations:

|  | Example III | Example IV |
|---|---|---|
| Temperature of stock into exchanger (° C) | 102 | 105 |
| Feed rate of stock (kg/hr m²) | 434 | 624 |
| Temperature of stock exiting exchanger (° C) | 90 | 90 |
| Temperature of cooling water (° C) | 72 | 81 |
| Back pressure (atm.) | 5.8 | 12.2 |

-continued

|  | Example III | Example IV |
|---|---|---|
| Shear (joules/kg) | 48,000 | 44,000. |

Employing the above conditions crystalline 2,2-bis[3,5-dibromo-4-(2-hydroxyethoxy)phenyl] propane was produced and the resulting products could be stored for prolonged periods of ambient conditions without slumping, that is, losing their flowability.

In both of the above examples the diethoxylate content of the product was greater than 90%. Crystallization was not possible using a product containing 75% diethoxylate with 25% mono-, tri- and higher ethoxylated products.

To demonstrate the inability to obtain crystallization when the shear and temperature conditions are not within the defined limits molten (150° C) 2,2-bis[3,5-dibromo-4-(2-hydroxyethoxy)phenyl] propane (90% diethoxylate) was fed into the exchanger at a rate of 27.2 kg/hr but without any back pressure. While the temperature of the melt was reduced to 110° C the product was not crystallized even after aging the material at 60° C for two or three days.

We claim:

1. A process for crystallizing 2,2-bis[3,5-dibromo-4-(2-hydroxyethoxy)phenyl] propane containing at least 85% by weight of the diethoxylated product of the formula

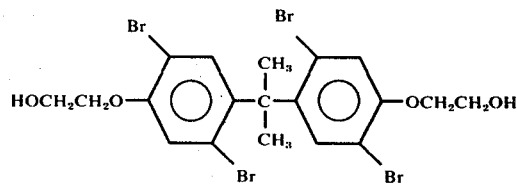

and less than 1% by weight solvent and water impurities which comprises applying a shear force of 25,000 and 60,000 joules per kilogram to a 105° to 120° C melt of said product for a period of at least 0.5 minute while lowering the temperature of the melt 15 to 30° C.

2. The process of claim 1 wherein a shear force of 35,000 to 57,000 joules per kilogram is applied over a period of about 1 to 5 minutes.

3. The process of claim 1 wherein the 2,2-bis[3,5-dibromo-4-(2-hydroxyethoxy)phenyl] propane is removed from the cooling and shear environment prior to complete crystallization and the temperature of the crystallizing product is 85°–105° C.

4. The process of claim 3 wherein the cooling and shear is effected by continuously feeding the 2,2-bis[3,5-dibromo-4-(2-hydroxyethoxy)phenyl] propane through a scrapped surface heat exchanger at a rate of 400 to 1110 kg/hr. m² of cooling surface while developing an internal pressure of 2 to 17 atmospheres.

5. The process of claim 4 wherein the 2,2-bis[3,5-dibromo-4-(2-hydroxyethoxy)phenyl] propane is fed at a rate of 450 to 700 kg/hr. m² of cooling surface and the internal pressure is between about 3 and 14 atmospheres.

6. The process of claim 5 wherein the processed 2,2-bis[3,5-dibromo-4-(2-hydroxyethoxy)phenyl] propane is spread on a continuously moving belt, cooled to 50° C or below, flaked and aged to 50° to 70° C to complete the crystallization.

* * * * *

UNITED STATES PATENT OFFICE
CERTIFICATE OF CORRECTION

Patent No. 4,002,688   Dated January 11, 1977

Inventor(s) B. L. Loeb and K. J. Witsken   Page 1 of 2

It is certified that error appears in the above-identified patent and that said Letters Patent are hereby corrected as shown below:

Column 2, line 38, "ebmodiment" should read --- embodiment ---.

Column 3, lines 20-28, the structural formula

"   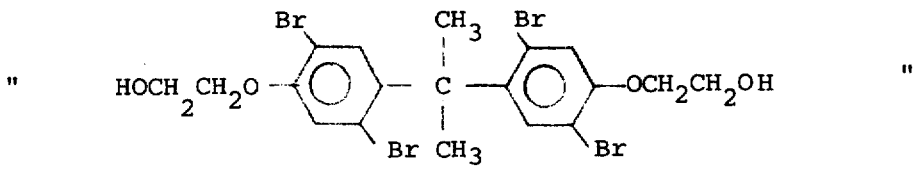   "

should read

---   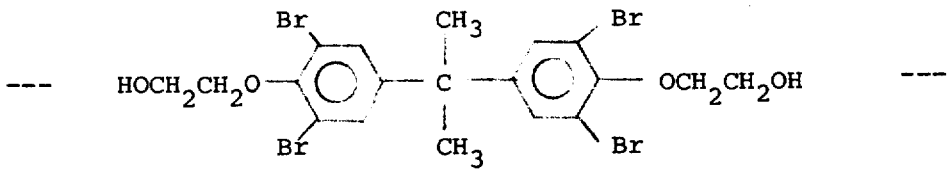   ---

Column 4, line 15, "crystalliaztion" should read --- crystallization ---.

Column 6, line 57, "closed" should read --- cooled ---.

UNITED STATES PATENT OFFICE
CERTIFICATE OF CORRECTION

Patent No. 4,002,688                    Dated January 11, 1977

Inventor(s) B. L. Loeb and K. J. Witsken            Page 2 of 2

It is certified that error appears in the above-identified patent and that said Letters Patent are hereby corrected as shown below:

Column 8, lines 31-39, in Claim 1 the structural formula

"  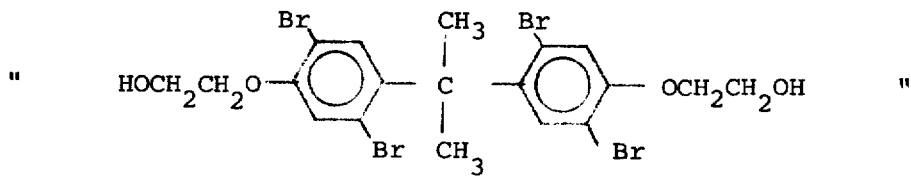  "

should read

---  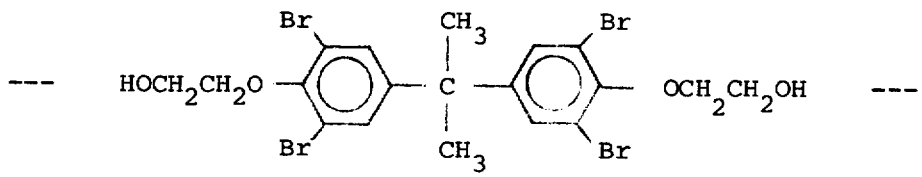  ---

Signed and Sealed this

*Twenty-fifth* Day of *October 1977*

[SEAL]

*Attest:*

RUTH C. MASON
*Attesting Officer*

LUTRELLE F. PARKER
*Acting Commissioner of Patents and Trademarks*